(12) United States Patent
Winkler

(10) Patent No.: US 6,238,374 B1
(45) Date of Patent: May 29, 2001

(54) HAZARDOUS FLUID INFUSER

(75) Inventor: Rance A. Winkler, Atlanta, GA (US)

(73) Assignee: Proxima Therapeutics, Inc., Alpharetta, GA (US)

( * ) Notice: Subject to any disclaimer, the term of this patent is extended or adjusted under 35 U.S.C. 154(b) by 0 days.

(21) Appl. No.: 09/369,903

(22) Filed: Aug. 6, 1999

(51) Int. Cl.⁷ .................................................. A61M 25/00
(52) U.S. Cl. ............................ 604/256; 604/257; 604/905
(58) Field of Search ............................ 604/256, 275, 604/82, 85, 83, 131, 141, 905

(56) References Cited

U.S. PATENT DOCUMENTS

| | | | |
|---|---|---|---|
| 4,804,366 | 2/1989 | Zdeb et al. | 604/85 |
| 4,850,978 | 7/1989 | Dudar et al. | 604/201 |
| 4,966,588 | 10/1990 | Rayman et al. | 604/165 |
| 5,074,844 | 12/1991 | Zdeb et al. | 604/83 |
| 5,120,324 | 6/1992 | Sancoff | 604/283 |
| 5,192,272 | 3/1993 | Faure | 604/141 |
| 5,207,667 | 5/1993 | Walker et al. | 604/905 |
| 5,308,334 | 5/1994 | Sancoff | 604/131 |
| 5,578,005 | 11/1996 | Sancoff et al. | 604/82 |
| 5,807,337 | 9/1998 | Yamada et al. | 604/143 |

*Primary Examiner*—John D. Yasko
(74) *Attorney, Agent, or Firm*—Thomas J. Engellenner; Ronald E. Cahill; Nutter, McClennen & Fish, LLP

(57) ABSTRACT

An infuser for transferring hazardous treatment fluids to and from a medical application includes a spill containing housing having a medical application connecting element and a syringe seat. The syringe seat of the infuser leads to a syringe connecting element that provides a fluid coupling between the syringe and a fluid passage leading to the medical application connecting element. The interior of the housing can be sealed against leaks, for example, by providing the housing in two portions with a gasket provided between the portions. A fluid tight coupling between the syringe and the interior of the housing may be created by integrally forming a septum with the gasket and coupling the syringe with the syringe connecting element through the septum. The infuser can also be provided with two syringe seats so that two different fluids can be transferred. In one embodiment, a second syringe connecting element is provided in fluid-tight communication with a second fluid passage. A method for transferring fluids to and from a medical application is also disclosed.

17 Claims, 3 Drawing Sheets

HAZARDOUS FLUID INFUSER

BACKGROUND OF THE INVENTION

The invention relates generally to methods and associated apparatus for controllably delivering radioactive or cytotoxic fluids for medical application, and specifically to methods and associated apparatus for the infusion of radioactive fluids for medical application, such as a liquid containing a radioisotope or biologically active substance.

In many medical applications it is necessary or desirable to administer amounts of radioactive fluids or medicines and other pharmaceutical fluids to a patient's body. For example, I-131 is administered to a patient in need of radiotherapy or I-125 for diagnostics. Other medicines that may be administered include radiosensitizers, chemotherapy, biologically active substances, and cytotoxics.

Certain of these applications involve infusing the fluid directly into a patient, such as through an intravenous tube or through direct application of the fluid to a specific portion of the patient's anatomy needing treatment or being subject to diagnostic procedures. Other medical applications involve infusing the fluid to a medical device located within or in proximity to the patient. An example of this type of application is illustrated in Williams U.S. Pat. No. 5,611,767. Williams shows an implantable balloon that can be filled with radioactive, chemotherapeutic or other fluids for treatment of marginal cancerous tissue remaining after surgical resection of a cancerous tumor. As further illustrated in Williams, fluids may be infused into the device, for example, by hypodermic syringe (FIG. 4 of U.S. Pat. No. 5,611,767) or by a transdermal catheter (FIG. 8 of U.S. Pat. No. 5,611,767). Even where a transdermal catheter is used, a hypodermic syringe is typically used to infuse the required fluid through the catheter.

Particularly in the case of radioactive fluid syringe injections, current methods of syringe shielding may not provide the patient or the medical practitioner with the total protection needed in terms of radiation shielding or containment of a spill or leak of the infusion system apparatus. Radioactive fluids are typically supplied to a balloon such as those illustrated in Williams, for a specified period of time. The fluid is then removed from the balloon and the balloon can be flushed with saline or some other non-hazardous dilutant before further surgery to remove the balloon from the patient's body. The infusion, removal and flushing of the radioactive fluid results in the use of several syringes which must be interchanged in the infusion system with a resulting increase in the possibility that radioactive fluids will leak or spill.

Syringe shields are currently available and are generally made to shield a syringe filled with radioactive fluids by employing lead (Pb) as a means of shielding the radioactivity. These devices, however, generally protect patients and medical personnel only from radioactive fluids within the body of the syringe, but do not provide adequate shielding and containment of possible leaks or spills of the infusion system.

SUMMARY OF THE INVENTION

The invention provides an infuser for transferring hazardous treatment fluids to and from a medical application while protecting both patients and healthcare providers from potentially dangerous spills and leaks. The infuser includes a spill containing housing having a medical application connecting element and a syringe seat. The syringe seat of the infuser leads to a syringe connecting element that provides a fluid coupling between the syringe and a fluid passage leading to the medical application connecting element. The interior of the housing can be sealed against leaks, for example, by providing the housing in two portions with a gasket provided between the portions. A fluid tight coupling can be formed between the syringe and the interior of the housing by integrally forming a septum with the gasket, and coupling the syringe with the syringe connecting element through the septum. The infuser can thus transfer hazardous fluids from one or more syringes to a medical application with little or no risk of leaks or spills.

The infuser of the invention can also be provided with two syringe seats so that two different fluids can be transferred. This configuration is particularly useful where the hazardous fluid must be diluted or flushed. In one embodiment, a second syringe connecting element is provided in fluid-tight communication with a second fluid passage. The second fluid passage may connect to the first fluid passage in proximity to the first syringe connecting element, allowing fluid from the second syringe to flush out both fluid passages.

The infuser of the invention may also be shielded against radiation to prevent harm to patients and healthcare providers from radioactive materials within the infuser, whether within the fluid passages or generally within the sealed housing. The housing may also be provided with a fluid absorbing material to further control any leaked or spilled fluids within the housing. In addition, a unidirectional valve can be placed in the second fluid passage to prevent hazardous fluids from backing up from the first fluid passage to an unshielded syringe at the second syringe seat.

The invention also includes a method for transferring hazardous fluids to a medical application using an infuser of the invention having two syringe seats. The method involves placing a first syringe containing a therapeutic fluid in fluid communication with the first syringe connecting element; delivering a dosage of the therapeutic fluid to the medical application; placing a second syringe containing a filling fluid in fluid communication with the second syringe connecting element; and delivering an amount of filling fluid to the medical application. The method can include removing the therapeutic fluid from the medical application as well.

BRIEF DESCRIPTION OF THE DRAWINGS

The invention will be more fully understood from the following detailed description taken in conjunction with the accompanying drawings, in which.

DETAILED DESCRIPTION OF THE DRAWINGS

Figure 1:
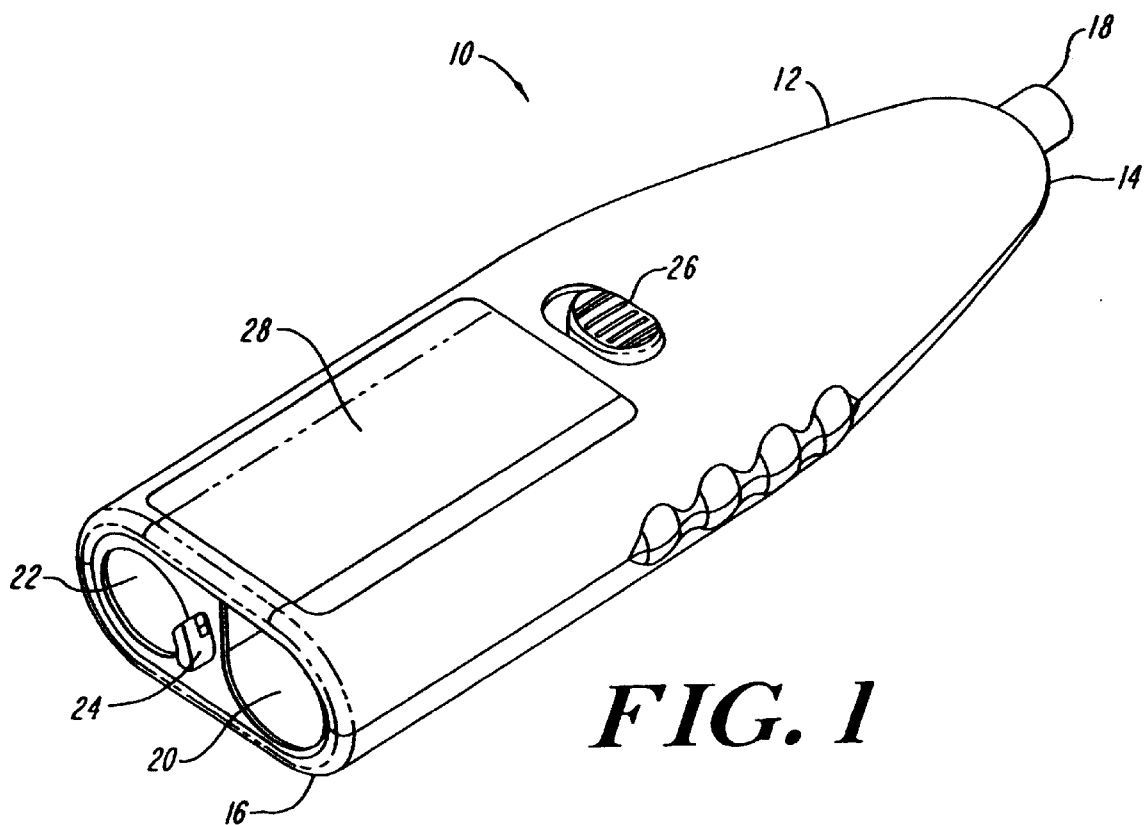
FIG. 1 shows a perspective view of a hazardous fluid infuser of the invention.

FIG. 1 illustrates an infuser 10 of the invention for transferring a hazardous treatment fluid from a syringe to a medical application. The infuser 10 includes an outer housing 12 having a first end 14 and a second end 16. A medical application connecting element 18 is provided on the first end 14 of housing 12. The medical application connecting element 18 may be a threaded connector, a Luer locking element, or some other connecting element useful for providing a sealed fluidic coupling. First and second syringe openings 20, 22 are provided at the second end 16 of housing 10. The first syringe opening 20 is shaped to accept a syringe having radiation shield. The second syringe opening has a locking element 24 provided adjacent to opening 22 on housing 12 to lock a second syringe into the second syringe opening 22. A biased button 26 is provided on housing 12 for releasably locking a radiation shielded syringe in the first syringe opening 20. A window 28 can also be provided on housing 12 to allow a user of infuser 10 to view the syringe or syringes seated in the infuser to ascertain the amount of fluid remaining therein.

Figure 2:
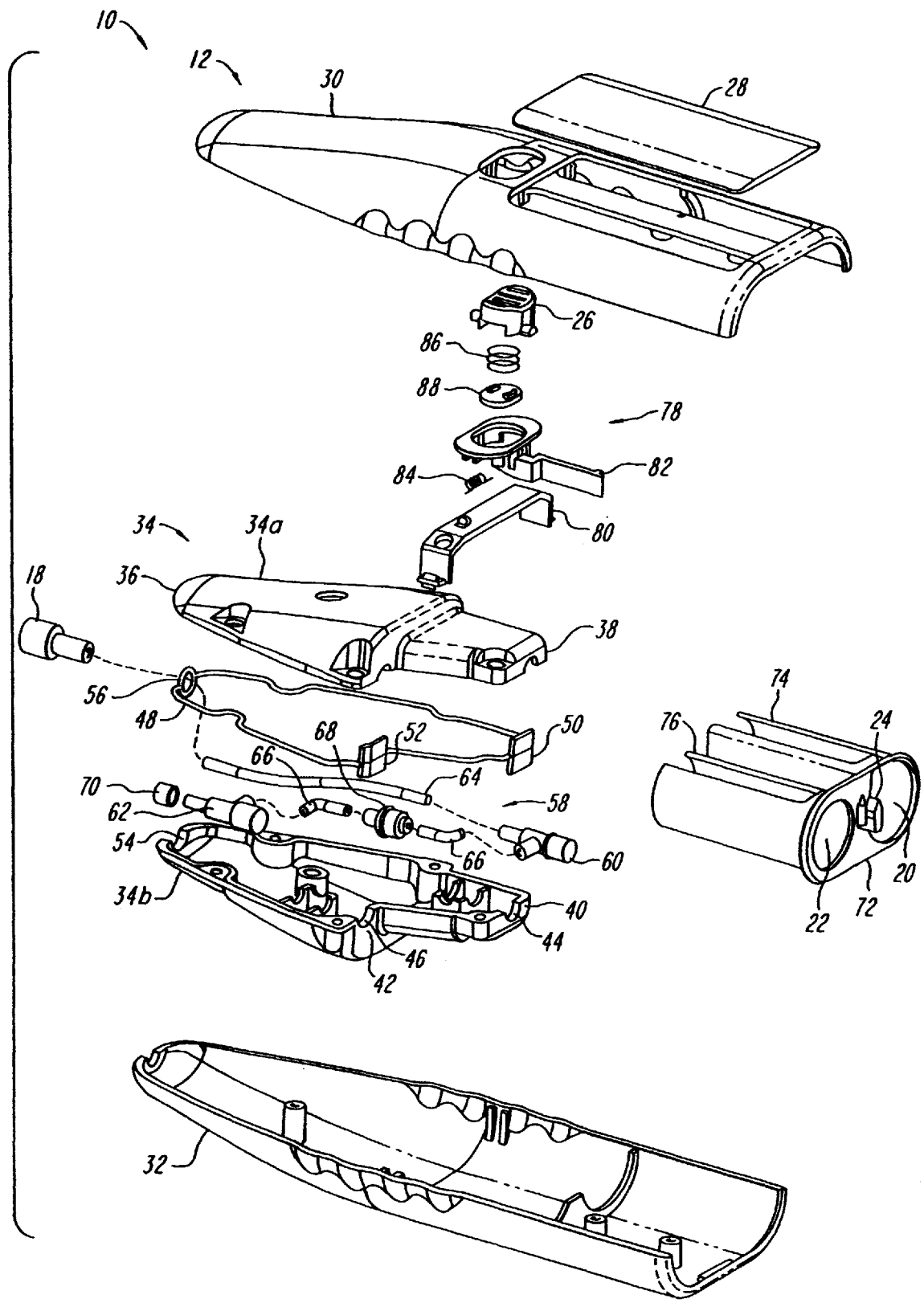
FIG. 2 shows an exploded view of the infuser of FIG. 1.

An exploded view of the infuser 10 is provided in FIG. 2. As shown in FIG. 2, housing 12 is provided in top 30 and bottom 32 portions with window 28 fitting into the top portion 30 of the housing. An inner housing having top and bottom portions 34a, 34b is provided (the combined top and bottom portions 34a, 34b hereinafter "inner housing 34") inside housing 12.

Inner housing 34 has a first end 36 and a second end 38, with a first syringe seat 40 and a second syringe seat 42 provided on the second end. The first syringe seat 40 defines a first syringe entry port 44 and the second suture seat 42 defines a second syringe entry port 46. A gasket 48 fitted and designed to form a fluid tight seal between the top and bottom portions 34a, 34b of the inner housing includes a first septum 50 and a second septum 52 corresponding to the first syringe entry port 44 and the second syringe entry port 46, respectively. While septums 50, 52 need not be integrally formed with gasket 48, forming them integrally as shown provides improved sealing characteristics for containing any spilled or leaked fluids within the sealed inner housing 34. Alternatively, a septum could be provided on each of the entry ports 44, 46 and the interface between the ports 44, 46 and inner housing 34 is sealed.

Inner housing 34 has a medical application connecting element port 54 defined on its first end 36 and gasket 48 has a corresponding medical application connecting element sealing feature 56 which forms a seal to inner housing 34 around port 54. When 20 configured in this manner, inner housing 34 is completely sealed except for the medical application connecting element port 54 which must be open to allow a fluidic connection through medical application connecting element 18 to the medical application to which the infuser 10 is directed.

Infuser 10 includes an injection tubing set 58 within inner housing 34 for transmitting fluids to be infused from the syringe ports 44, 46 to the medical application connecting element 18. Tubing set 58 includes a first injection port 60 located proximate to the first syringe entry port 44 and a second injection port 62 located proximate to the second syringe entry port 46. Each injection port 60, 62 can include a needle guiding means such as angled sidewalls to guide a syringe needle to the center of the port so as to reduce the risk that the needle will puncture any tubing connected to the injection port.

The first injection port 60 leads to a fluid passage, such as tube 64 which extends directly to medical application connecting element 18.

The second injection port 62 leads to a fluid passage, such as tubes 66, which connects to the first injection port 60 or to tube 64 extending from the first injection port at a location proximate to the port. In this way, the second injection port 62 provides a fluid passage to the medical application connecting element 18 through tubes 66 and 64.

This fluid path allows for fluids entering the tubing set 58 from the second injection port 62 to flush the entire tubing set 58 including tube 64. In addition, a one-way valve 68 can be added to tubes 66 to prevent possible flows of hazardous fluids in tube 64 to a syringe seated at the second syringe seat 42. A needle resistant cap 70 can be placed on the second injection port 62 to prevent a syringe needle from extending too far through the second injection port and causing a spill.

While the embodiment depicted in FIG. 2 shows an inner housing 34 enclosed within an outer housing 12, the objects of the present invention can be met by employing a single housing. For example, inner housing 34 could be used alone or with features from housing 12 added to it. Similarly housing 12 could be used alone, for example, by providing certain features from inner housing 34, such as gasket 48 and tubing set 58, with housing 12.

At least one housing, preferably inner housing 34 in infuser 10 of FIG. 2, can be provided with radiation shielding. One way to provide radiation shielding is to construct the top and bottom portions 34a, 34b of inner housing 34 from a material that is opaque to radiation such as lead, magnesium, a moldable thermoplastic material having a density equal to lead, or other materials known to be resistant to radiation. When combined with a radiation shielded syringe, this combination of materials can provide radiation shielding from the syringe up to the medical application to which the radioactive fluid is being delivered including shielding of any spills or leaks in the tubing set 58 or resulting from a misapplication of a syringe. In addition, an absorbent material such as a dessicate or a compressed sponge can be placed inside inner housing 34 to absorb any spillage or leaked fluids.

Housing 12 can include a syringe holder 72 having first and second sidewalls 74, 76 that define first and second syringe openings 20, 22 and that guide and help positively seat syringes at the first and second syringe seats 40, 42. Syringe holder 72 can be provided as a separate part as illustrated, or it can be integrally formed with either housing 12 or inner housing 34.

Housing 12 can further include a biased locking mechanism 78 for engaging a syringe located at the first syringe seat 40 to prevent accidental or unintended movement of a syringe containing a hazardous fluid. As illustrated, biased locking mechanism 78 rests on and is guided by locking seat 80 which is attached to housing 12. The locking mechanism 78 includes an engagement element 82 for attachment to a syringe to prevent movement of the syringe and a thumb switch 26 operable from outside the housing 12 to unlock the biased locking mechanism 78. The biased locking mechanism 78 can be biased by spring 84 so that engagement element 82 locks a syringe into place automatically upon placement of a syringe a first syringe seat 40. In the exemplary embodiment, thumb switch 26 itself is biased using spring 86 and plate 88 so that the thumb switch must be depressed before being moved to an unlocked position to release a locked syringe.

Figure 3:
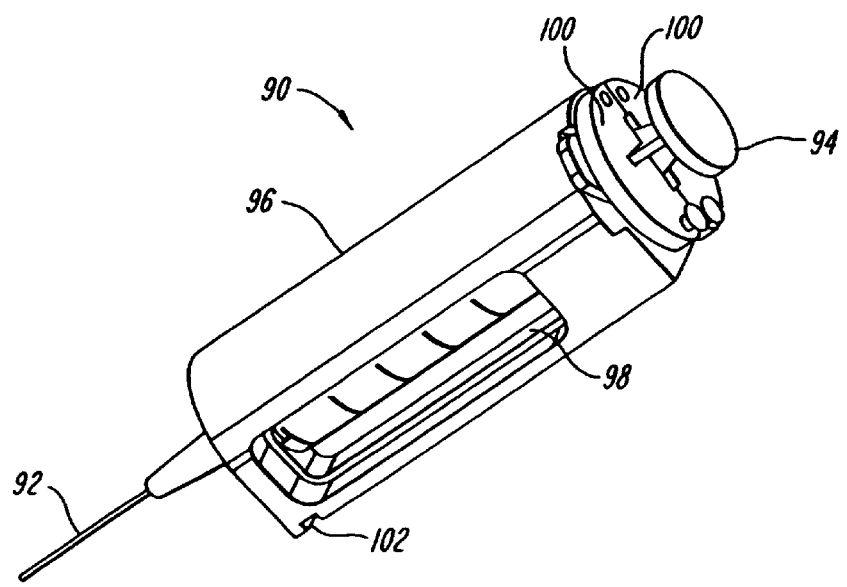
FIG. 3 illustrates a shielded syringe useful with the infuser of FIG. 1.

A shielded syringe 90 useful with the infuser 10 of the invention is illustrated in FIG. 3. Shielded syringe 90 is generally provided as a standard syringe having a needle 92, a plunger 94, and a radiation shield 96 provided about its barrel. The radiation shield 96 can be formed from any of the radiation resistant materials discussed above for providing radiation shielding for inner housing 34. Alternatively, the syringe barrel itself could be formed from a material such as a thermoplastic polymer/composite having radiation resistant qualities, and thus eliminate the need for a separate shield. Radiation shield 96 includes a window 98 formed of material that is translucent to visible light but opaque to radiation such as leaded glass. Radiation shield 96 also includes two rotating members 100 that come together to define a cruciform opening suitable to shield around plunger 94. Rotating the sliding members to an open and apart position allows a used syringe to be removed from shield 96 and a new syringe to be inserted. Radiation shield 96 can also include a locking depression 102 that mates with engagement element 82 (FIG. 2) to lock shielded syringe 90 into place at first syringe seat 40 during use.

Figure 3A:
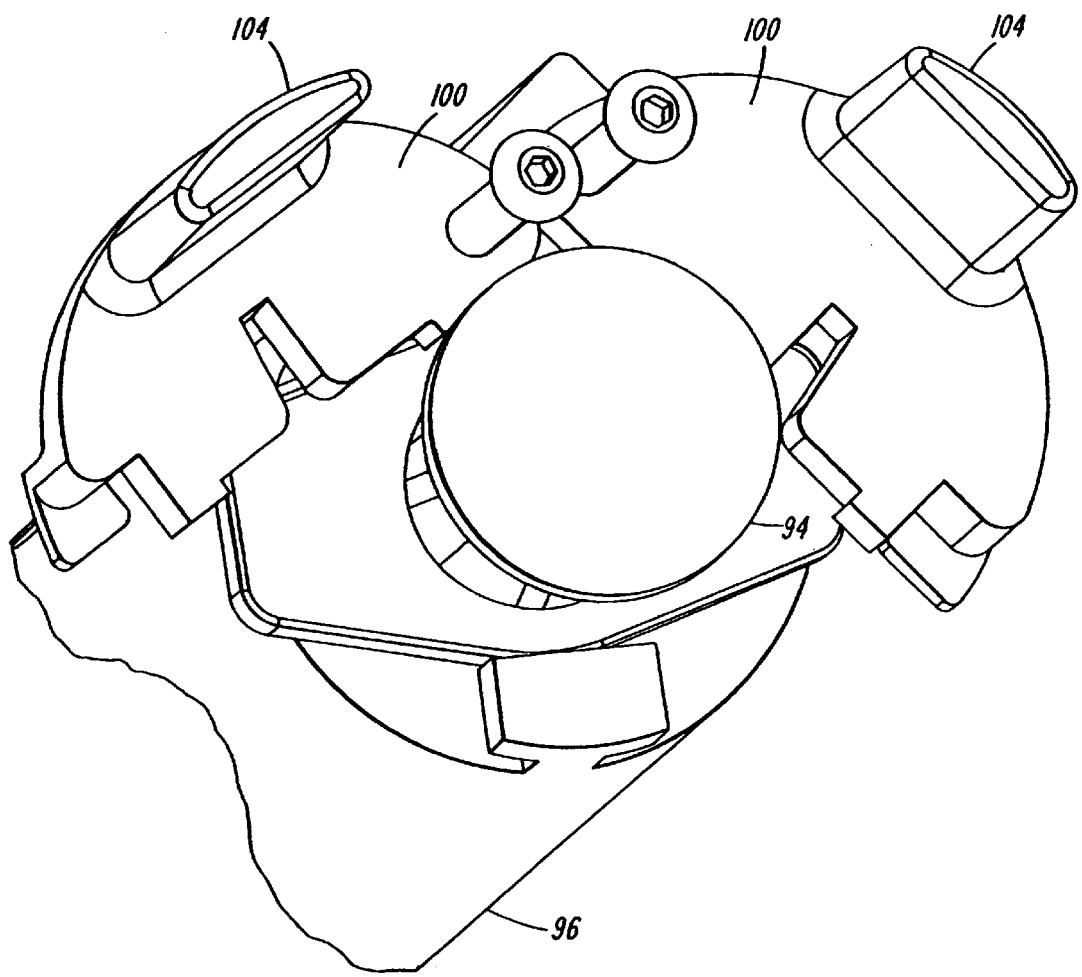
FIG. 3A illustrates an additional embodiment of the syringe of FIG. 3.

In addition, rotating members 100 may include one or more catch members 104 (FIG. 3A). Catch member 104 may included a biased latch that closes on the syringe plunger 94 when the plunger is fully depressed to prevent "backing out" of the plunger, or catch member 104 can cause a friction fit between the plunger and the catch member for the same purpose. Alternatively, an additional rotating member (not shown) may also be provided that rotates behind plunger 94 after it has been depressed to prevent plunger 94 from "backing out."

Infuser 10 can be used to infuse radioactive fluids into an inplanted balloon, such as the balloon of U.S. Pat. No. 5,611,767 for example, for use in providing brachytherapy treatment to a patient as follows. A shielded syringe, such as syringe 90, is loaded with a material containing a predetermined radionuclide, for example, I-125, I-131, Yb-169 or other source of radiation, such as radionuclides that emit photons, beta particles, gamma radiation, or other therapeutic rays. The radioactive material contained within syringe 90 can be a fluid made from any solution of radionuclide(s), e.g., a solution of I-125 or I-131. A radioactive fluid can also be produced using a slurry of a suitable fluid containing small particles of solid radionuclides, such as Au-198, Y-90. Moreover, the radionuclide(s) can be embodied in a gel. One radioactive material useful in the invention is Iotrex™, a sterile single use, non-pyrogenic solution containing sodium 3-($^{125}$ I)iodo-4-hydroxybenzenesulfonate ($^{125}$-HBS), available from Proxima Therapuetics, Inc. of Alpharetta, Ga.

In typical applications, the balloon receiving the radioactive fluid will have a diameter of 2 cm (volume of 5 cc), 3 cm (volume of 15 cc), or 4 cm (volume of 35 cc). Iotrex™ has an activity of approximately 150 mCi/cc, and shielded syringe 90 is a 5 cc syringe which can deliver desired doses of 1, 2, or 3 cc of Iotrex™ to the balloon. Once filled with the appropriate amount of radioactive fluid, shielded syringe 90 is inserted into first syringe opening 20 of infuser 10 so that needle 92 pierces first septum 50 and engages first injection port 60. Shielded syringe 90 can be inserted until the syringe meets first syringe seat 40 and locking mechanism 78 engages the syringe shield 96. Radioactive fluid can then be delivered to the balloon as appropriate and the level of fluid in syringe 90 can be viewed through windows 28 and 98. When shielded syringe 90 is removed from infuser 10, first septum 50 provides a wiping action on needle 92 to insure that any radioactive material remaining on the needle after its removal from first injection port 60 is kept within shielded inner housing 34.

In this example, syringe plunger 94 provides the force on the syringe fluid reservoir to expel the syringe reservoir's contents. However, other means for fluid delivery, e.g., a needle-free or needleless syringe with the tubing set being in fluid communication with the syringe fluid reservoir may also be employed. The apparatus may further include a pump control mechanism so that delivery or retrieval of the fluid can be controlled.

A second syringe (not shown), typically a standard 20 cc syringe, can be employed to supply a saline solution to fill the requisite volume of the balloon not filled with radioactive fluid. For example, if a 3 cm (volume of 15 cc) diameter balloon is deployed and 2 cc of Iotrex™ provides the desired therapeutic dose of radiation, 13 cc of a fluid such as saline is required to fully inflate the balloon. The second syringe is inserted into second syringe opening 22 of infuser 10 so that the syringe needle pierces second septum 52 and engages second injection port 62. The syringe can be inserted until the syringe meets second syringe seat 42, and fluid can then be delivered to the balloon as appropriate. The level of fluid in the syringe can be viewed through window 28. Because of the arrangement of tubing set 58, the saline fluid tends to flush out any remaining radioactive material in tubing set 58 and deliver it to the balloon with the saline fluid. Generally, the timing of filling fluid delivery is not limited and the filling fluid may be added before the therapeutic fluid is delivered, after the therapeutic fluid is delivered, or after some of the therapeutic fluid is delivered.

Where more filling fluid is required, the saline syringe may be removed from the second syringe seat 42 and replaced with another syringe. For example, where a 4 cm balloon (volume of 35 cc) is used with 3 cc of Iotrex™, a single 20 cc syringe of saline is insufficient to fill the balloon to the required volume. In this case, the saline syringe can be removed, refilled, and redeployed in infuser 10, or a second saline syringe may be used to provide the desired volume of filling fluid.

Typically, the radioactive fluid is left in place in the balloon for a time sufficient to result in an overall dose of radiation to target tissue in proximity to the balloon that is within a prescribed range. By way of example, in one application a prescribed dose may be on the order of 60 Gray, and it may take approximately three to five days to deliver this dose. In the time that the dose is being delivered, the infuser may remain connected to the patient as described above, or it may be disconnected and reconnected after the prescribed dose has been delivered in order to remove the radioactive fluid.

After the radioactive fluid has been in place for the desired amount of time to result in a prescribed radiation dosage, the fluid containing radioactive material is removed from the balloon and the balloon may be flushed, typically with saline, and removed from the patient. The radioactive fluid can be removed from the balloon by deploying a shielded syringe at the first syringe seat 40 and withdrawing the fluid using as many syringes as necessary to remove all of the fluid. A saline syringe can be deployed at the second syringe seat 42 to flush the balloon with saline. After the balloon has been flushed and all of the fluids removed, medical application connecting element 18 can be disconnected, and the infuser removed.

Inner housing 34 and syringe holder 72 are configured to work with a heavily shielded 5 cc syringe at the first syringe seat 40 and an unshielded 20 cc syringe at the second syringe seat 42. A person of ordinary skill in the art will recognize that other configurations are possible within the scope of the invention. For example, infuser 10 could be configured to accept a lightly shielded 20 cc syringe at the first syringe seat 40. This configuration would be particularly useful for flushing a balloon and removing the fluids contained therein. Because the radioactive fluid would be diluted, heavy shielding would not be necessary, and using a larger syringe would allow for more rapid removal of fluids with fewer syringe changes. It is thus possible to use two infuser 10 devices, one to inject hazardous fluids and a second for flushing and removal of fluids, or a single infuser 10 can be employed as described above. In addition, inner housing 34 and syringe holder 72 can be replaceable, allowing one configuration for infusion and a second configuration within the same outer housing 12 for removal.

As shown in the described example, the infusion and removal of hazardous fluids to and from a medical application can involve many fluid exchanges and the use of several delivery instruments. The infuser of the invention provides a safe and reliable device for delivering and removing these fluids while ensuring that any spills or leaks are contained in a shielded, fluid-tight housing so that patients and medical personnel are not exposed to hazardous fluids. While the example described herein illustrates the use of the infuser with a radioactive fluid, the infuser may be used with radiosensitizers, chemotherapy, biologically active substances, cytotoxics and other hazardous medicines.

As used herein, the term "biologically active substance" means all types of medical and biological fluid used in the treatment of humans and animals including but not limited to peptides (such as insulin), analgesics, antiarrhythmics, steroids, hormones, nicotine, vitamins, anti-migraine medicine, anti-coagulants, local anesthetics, vaccines, allergens, muscle relaxants, etc.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An infuser for transferring a hazardous treatment fluid from a syringe to a medical application comprising:
   a spill containing housing having an interior sealed against fluid leaks, a first end and a second end;
   a medical application connecting element provided on the first end of the housing, the connecting element providing a fluidic coupling between the housing and the medical application;
   a syringe seat for positive seating of a syringe provided at the second end of the housing;
   a syringe connecting element located on the syringe seat and having a septum and a needle guiding means, the syringe connecting element providing a fluid-tight coupling between a needle of the syringe and the interior of the housing; and
   a fluid passage provided within the interior of the housing and extending from the syringe coupling element to the medical application connecting element.

2. The infuser of claim 1, wherein the spill containing housing comprises two portions with a gasket located between the two portions, the gasket and septum being integrally formed and sealing the housing against fluid leaks.

3. The infuser of claim 1, wherein the spill containing housing includes radiation shielding.

4. The infuser of claim 1, further comprising a second syringe seat and a second syringe connecting element having a second septum and a second needle guiding means, the second syringe connecting element being coupled to a second fluid passage in fluid communication with the medical application connecting element.

5. The infuser of claim 4, wherein the second fluid passage is coupled to the first fluid passage proximate to the first syringe connecting element so as to flush the first fluid passage when a fluid is delivered from the second syringe connecting element to the medical application connecting element.

6. The infuser of claim 5, wherein the first fluid passage includes a unidirectional valve that permits fluid flow from the second syringe connecting element to the fluid passage.

7. The infuser of claim 1, wherein the spill containing housing is removably and replaceably provided within an outer housing.

8. The infuser of claim 1, further comprising a syringe holder for guiding and positively seating a syringe at the syringe seat.

9. The infuser of claim 1, further comprising a locking mechanism for releasably locking a syringe to the syringe seat.

10. An infuser for delivering therapeutic fluids to or retrieving therapeutic fluids from a medical application comprising:
    a housing having a first end and a second end;
    a medical application connecting element provided on the first end of the housing, the connecting element providing a fluidic coupling between the housing and the medical application;
    a first syringe seat for positive seating of a syringe on the second end of the housing, the first syringe seat having a first syringe connecting element;
    a second syringe seat for positive seating of a syringe on the second end of the housing, the second syringe seat having a second syringe connecting element;
    a first fluid passage extending from the first syringe connecting element to the medical application connecting element; and
    a second fluid passage extending from the second syringe connecting element to the medical application connecting element.

11. The infuser of claim 10, wherein the second fluid passage is coupled to the first fluid passage proximate to the first syringe connecting element so as to flush the first fluid passage when a fluid is delivered from the second syringe connecting element to the medical application connecting element.

12. The infuser of claim 11, wherein the first fluid passage includes a unidirectional valve that permits fluid flow from the second syringe connecting element to the fluid passage.

13. The infuser of claim 10, wherein the housing is sealed against fluid leaks.

14. The infuser of claim 13, wherein the housing comprises two portions with a gasket provided between the two portions, the gasket including a first septum and a second septum, corresponding to the first and second syringe connecting elements, integrally formed therewith.

15. The infuser of claim 13, wherein the housing includes radiation shielding.

16. A method for delivering therapeutic fluids to a medical application comprising:
    a) providing an infuser for delivering therapeutic fluids to or retrieving therapeutic fluids from a medical application comprising:
       a housing having a first end and a second end;
       a medical application connecting element provided on the first end of the housing, the connecting element providing a fluidic coupling between the housing and the medical application;
       a first syringe seat for positive seating of a syringe on the second end of the housing, the first syringe seat having a first syringe connecting element;
       a second syringe seat for positive seating of a syringe on the second end of the housing, the second syringe seat having a second syringe connecting element;

a first fluid passage extending from the first syringe connecting element to the medical application connecting element; and
  a second fluid passage extending from the second syringe connecting element to the medical application connecting element;
b) placing a first syringe containing a therapeutic fluid in fluid communication with the first syringe connecting element;
c) delivering a dosage of the therapeutic fluid to the medical application;

d) placing a second syringe containing a filling fluid in fluid communication with the second syringe connecting element; and
e) delivering an amount of filling fluid to the medical application.

17. The method of claim 16, further comprising:
f) placing a third syringe in fluid communication with the first syringe connecting element; and
g) removing fluid from the medical application into the third syringe.

* * * * *

UNITED STATES PATENT AND TRADEMARK OFFICE
CERTIFICATE OF CORRECTION

| | |
|---|---|
| PATENT NO. | : 6,238,374 B1 |
| DATED | : May 29, 2001 |
| INVENTOR(S) | : Rance A. Winkler |

It is certified that error appears in the above-identified patent and that said Letters Patent is hereby corrected as shown below:

<u>Column 3,</u>
Line 39, reads: "When 20 configured" should read: -- When configured --.

Signed and Sealed this

Fifth Day of March, 2002

*Attest:*

*Attesting Officer*

JAMES E. ROGAN
*Director of the United States Patent and Trademark Office*